(12) United States Patent
Shimada (10) Patent No.: US 8,369,481 B2
(45) Date of Patent: Feb. 5, 2013

(54) X-RAY INSPECTION DEVICE

(75) Inventor: Masahiro Shimada, Shiga (JP)

(73) Assignee: Ishida Co., Ltd., Kyoto (JP)

( * ) Notice: Subject to any disclaimer, the term of this patent is extended or adjusted under 35 U.S.C. 154(b) by 212 days.

(21) Appl. No.: 12/791,478

(22) Filed: Jun. 1, 2010

(65) Prior Publication Data

US 2010/0310043 A1 Dec. 9, 2010

(30) Foreign Application Priority Data

Jun. 8, 2009 (JP) .................................. 2009-137207

(51) Int. Cl.
*G01N 23/04* (2006.01)
(52) U.S. Cl. ......................................................... 378/57
(58) Field of Classification Search .................... 378/57, 378/58, 208; 382/132
See application file for complete search history.

(56) References Cited

U.S. PATENT DOCUMENTS

| | | | | |
|---|---|---|---|---|
| 3,958,078 A | * | 5/1976 | Fowler et al. | 348/127 |
| 5,629,966 A | * | 5/1997 | Dykster et al. | 378/57 |
| 8,019,040 B2 | * | 9/2011 | Kabumoto et al. | 378/57 |
| 2006/0098773 A1 | * | 5/2006 | Peschmann | 378/57 |

FOREIGN PATENT DOCUMENTS

| | | |
|---|---|---|
| EP | 0355128 B1 | 1/1996 |
| JP | 2002-098653 A | 4/2002 |
| JP | 2003-65976 | 3/2003 |
| WO | WO-99/54717 A2 | 10/1999 |

OTHER PUBLICATIONS

Korean Office Action of the corresponding Korean Application No. 10-2010-0053737, dated Feb. 23, 2012.

* cited by examiner

*Primary Examiner* — Irakli Kiknadze
(74) *Attorney, Agent, or Firm* — Global IP Counselors, LLP (57) ABSTRACT

An X-ray inspection device includes an X-ray detecting unit, a determining unit, and an output unit. The X-ray detecting unit is configured and arranged to detect a level of X-rays passing through an article. The determining unit is configured to determine a state of the article based on a detection level of the X-rays detected by the X-ray detecting unit using a plurality of thresholds including a first threshold and a second threshold for a single determination criterion. The output unit is configured and arranged to output a result of determination made by the determining unit.

14 Claims, 12 Drawing Sheets

X-RAY INSPECTION DEVICE

CROSS-REFERENCE TO RELATED APPLICATIONS

This application claims priority to Japanese Patent Application No. 2009-137207, filed on Jun. 8, 2009. The entire disclosure of Japanese Patent Application No. 2009-137207 is hereby incorporated herein by reference.

BACKGROUND

1. Field of the Invention

The present invention relates to an X-ray inspection device for scanning articles with X-rays and detecting foreign objects in the articles.

2. Background Information

X-ray inspection devices or similar apparatuses have conventionally been used to detect foreign objects in articles. Such X-ray inspection devices are currently the subject of research and development efforts.

For example, JP-A 2002-098653 discloses an X-ray inspection device for inspecting articles being continuously conveyed, wherein the results of the inspection can be readily understood. More specifically, the X-ray inspection device according to JP-A 2002-098653 is an X-ray inspection device for using X-rays to inspect the state of a conveyed article. The X-ray inspection device includes an X-ray detecting device for detecting the state of the article using X-rays, a determining device for determining the state of the article based on a detection level according to the X-ray detecting device, an output device for outputting a result of determination made by the determining device, a memory for storing a threshold used by the determining device as a determination standard, a first display part for displaying a value based on the detection level as an area corresponding to the value, and a display controlling device for causing the first display part to display the threshold and the value based on the detection level.

SUMMARY

According to the X-ray inspection device in JP-A 2002-098653, the value based on the detection level, from which a determination is made; and the threshold, used as a determination standard, are displayed in the first display part. The first display part displays the value based on the detection level as an area corresponding to the value. The user of the device can therefore recognize with relative ease whether the value based on the detection level is closer to or further from the threshold. In particular, since the first display part displays the value based on the detection level as a corresponding area, the user can perceptually recognize the margin of determination or a similar parameter without reading a numerical value.

However, with X-ray inspection devices or similar devices, when foreign objects is present in the article, there is a difference in response between an instance where the foreign objects is dust and an instance where the foreign objects is a component from an assembly line.

In other words, in an instance where the foreign objects is dust or similar matter, the article must be removed from the assembly line, whereas in an instance where the foreign objects is a component from the assembly line, it is necessary to stop the production line and inspect devices used upstream (i.e., in a pre-process).

However, with regards to articles that are mass-produced in an assembly line, if the production line is stopped on every occasion where foreign objects are present, the production efficiency will be reduced. Even though it is possible to determine whether or not foreign object is present, it is very difficult for the user to always judge whether the foreign objects comprise dust or a component from the assembly line.

An object of the present invention is to provide an X-ray inspection device having a plurality of determination standards, the X-ray inspection device being capable of determining whether a foreign object exists in an article based on the determination standards.

Another object of the present invention is to provide an X-ray inspection device having a plurality of determination standards, the X-ray inspection device being capable of determining whether a foreign object exists in an article based on the determination standards, and to determine whether the foreign object might cause problems for a production line.

An X-ray inspection device includes an X-ray detecting unit, a determining unit, and an output unit. The X-ray detecting unit is configured and arranged to detect X-rays passing through an article. The determining unit is configured to determine a state of the article based on a detection level of the X-rays detected by the X-ray detecting unit using a plurality of thresholds including a first threshold and a second threshold for a single determination criterion. The output unit is configured and arranged to output a result of determination made by the determining unit.

BRIEF DESCRIPTION OF THE DRAWINGS

Referring now to the attached drawings which form a part of this original disclosure.

DETAILED DESCRIPTION OF EMBODIMENTS

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

An embodiment of the present invention will now be described with reference to the accompanying drawings.

Figure 1:
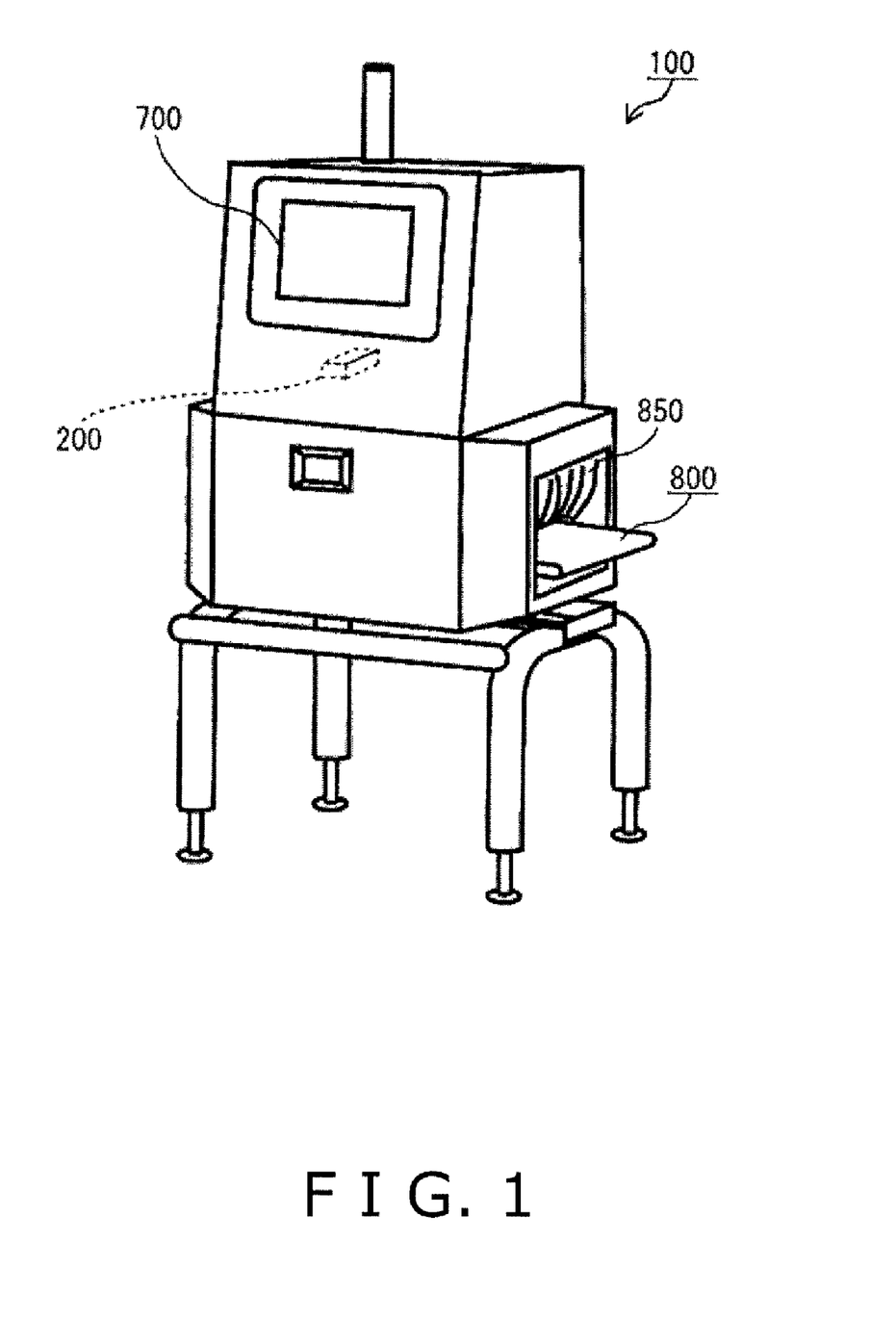
FIG. 1 is a schematic external view showing an example of an X-ray inspection device according to one embodiment of the present invention.
Figure 2:
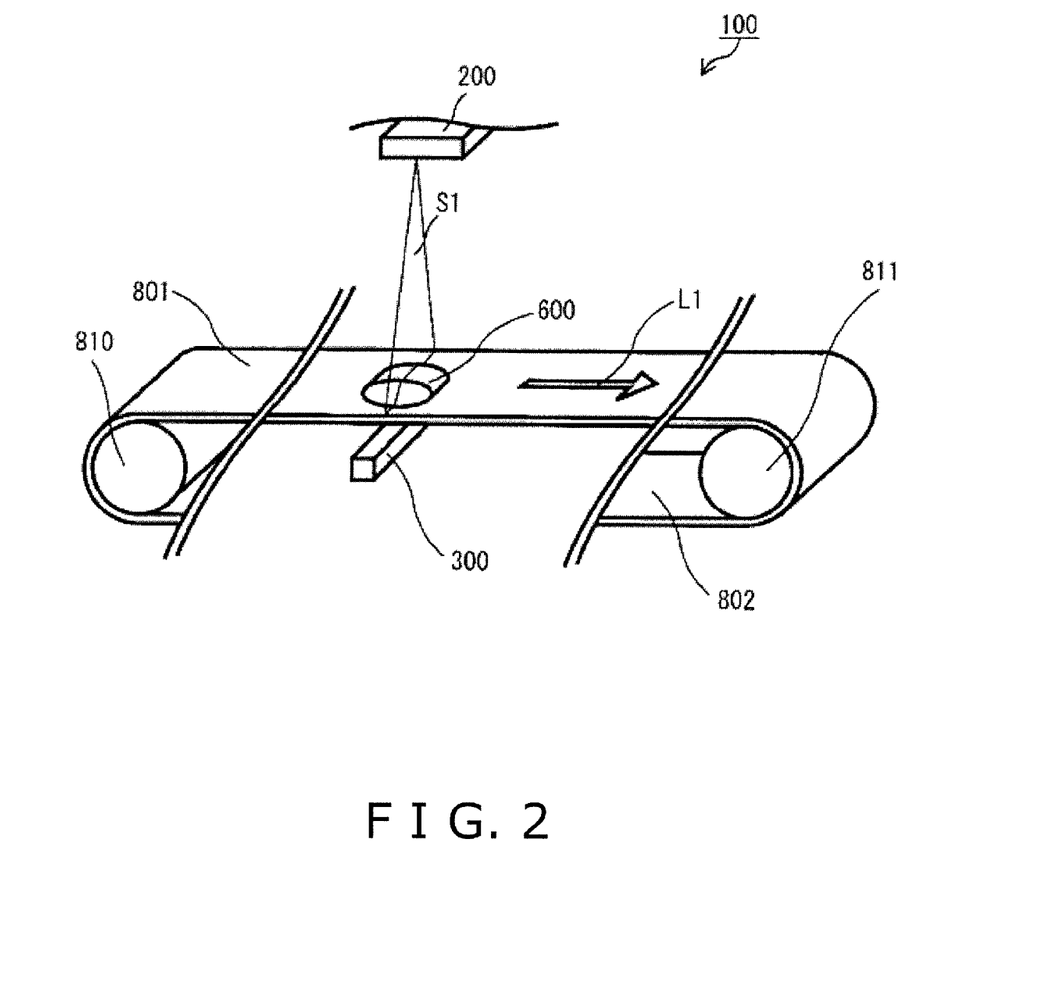
FIG. 2 is a schematic diagram showing an example of an internal structure of the X-ray inspection device according to the illustrated embodiment.

FIG. 1 is a schematic external view showing an example of an X-ray inspection device 100 according to one embodiment of the present invention, and FIG. 2 is a schematic diagram showing an example of an internal structure of the X-ray inspection device 100 according to the embodiment of the present invention.

As shown in FIG. 1, an X-ray emission device 200 is installed in the X-ray inspection device 100. An article 600 to be examined is placed on a conveyor belt 800 and transported through the X-ray inspection device 100, whereby an X-ray inspection is performed to examine whether the article contains foreign objects.

As shown in FIG. 1, the conveyor belt 800 of the X-ray inspection device 100 is formed so as to protrude outwards from the X-ray inspection device 100, and a plurality of X-ray shielding curtains 850 are provided in the vicinity of the protrusion. An operator operates a touch panel 700 to drive the X-ray inspection device 100. The touch panel 700 will be described in detail further below. An internal structure of the X-ray inspection device 100 will now be described.

As shown in FIG. 2, the X-ray inspection device 100 according to the present invention mainly comprises the X-ray emission device 200, a line sensor 300, and the conveyor belt 800. The conveyor belt 800 shown in FIG. 2 comprises an endless belt wrapped around a pair of rollers 810, 811. A portion of the belt travelling along a forward route is shown as a conveyor belt 801, and a portion of the belt travelling along a return route is shown as a conveyor belt 802. The line sensor 300 comprises a scintillator and a photodiode array (PDA). The line sensor 300 is provided between the conveyor belt 801 and the conveyor belt 802, and the X-ray emission device 200 is provided above the conveyor belt 801. In the depicted embodiment, the X-ray inspection device 100 includes only one single line sensor 300 that detects X-ray emissions emitted by the X-ray emission device 200.

The conveyor belt 801 transports the article 600 in the direction indicated by arrow L1, and the conveyor belt 802 travels in the direction opposite to that indicated by arrow L1. In other words, in the present embodiment, the X-ray inspection device 100 is configured so that damping of X-rays S1 is affected only by the conveyor belt 801, and is not dependent on the conveyor belt 802.

Figure 3:
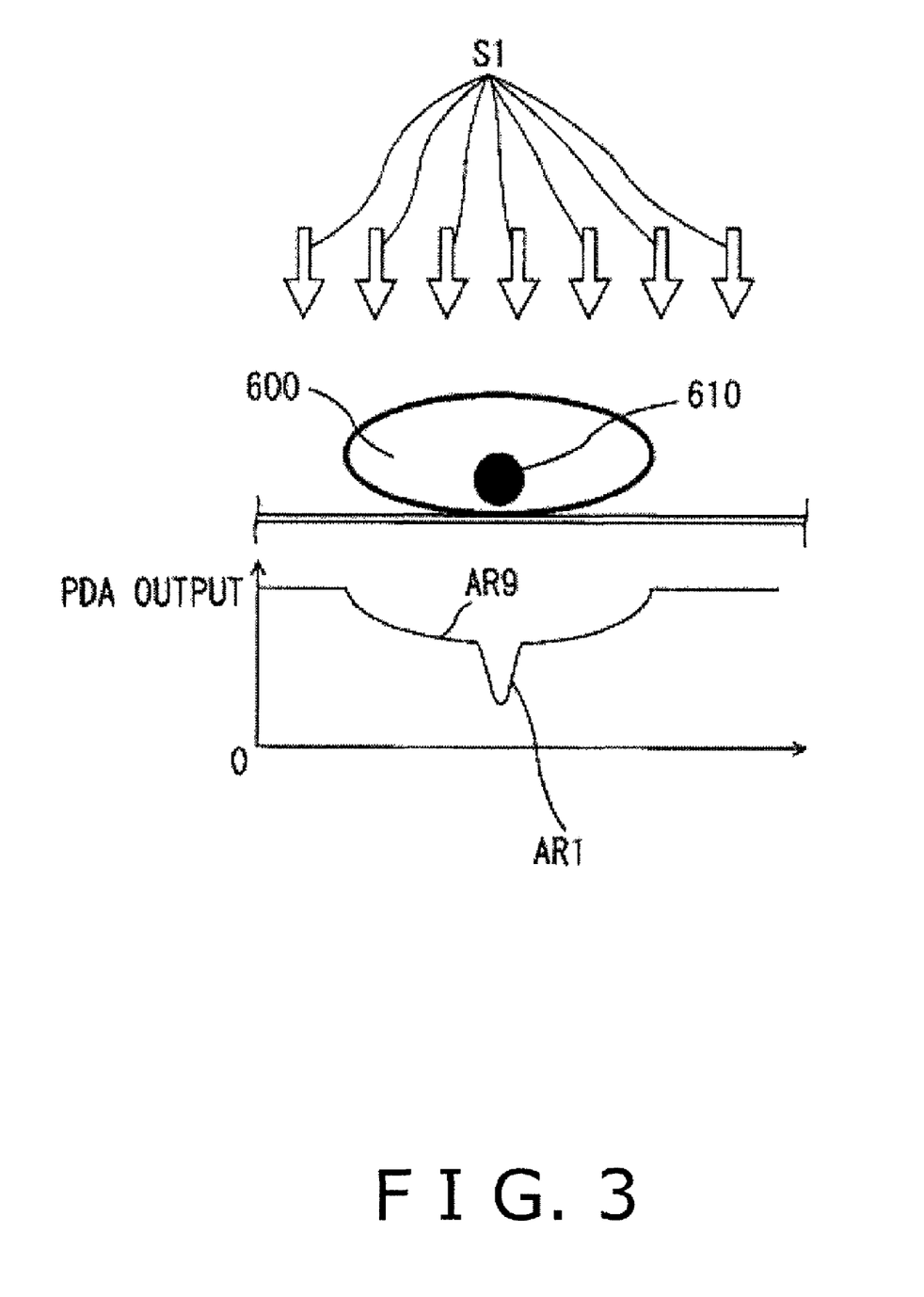
FIG. 3 is a schematic diagram illustrating a principle of inspection.

FIG. 3 is a schematic diagram illustrating a principle of X-ray inspection. The vertical axis represents an electrical signal output from the line sensor 300 (PDA OUTPUT), and the horizontal axis represents elapsed time.

As shown in FIG. 3, the conveyor belt 800 transports the article 600, whereby the X-rays S1 irradiate the entire article 600. Based on the level of the electrical signal output from the line sensor 300, an X-ray transmission image AR9 for an instance where the X-rays S1 pass through the article 600 is generated.

Specifically, as shown in FIG. 3, in an instance where the article 600 contains foreign objects 610, a foreign objects image AR1 appears in the X-ray transmission image AR9. In an instance where the article 600 does not contain the foreign objects 610, the foreign objects image AR1 does not appear; instead, only the X-ray transmission image AR9 appears.

Figure 4:
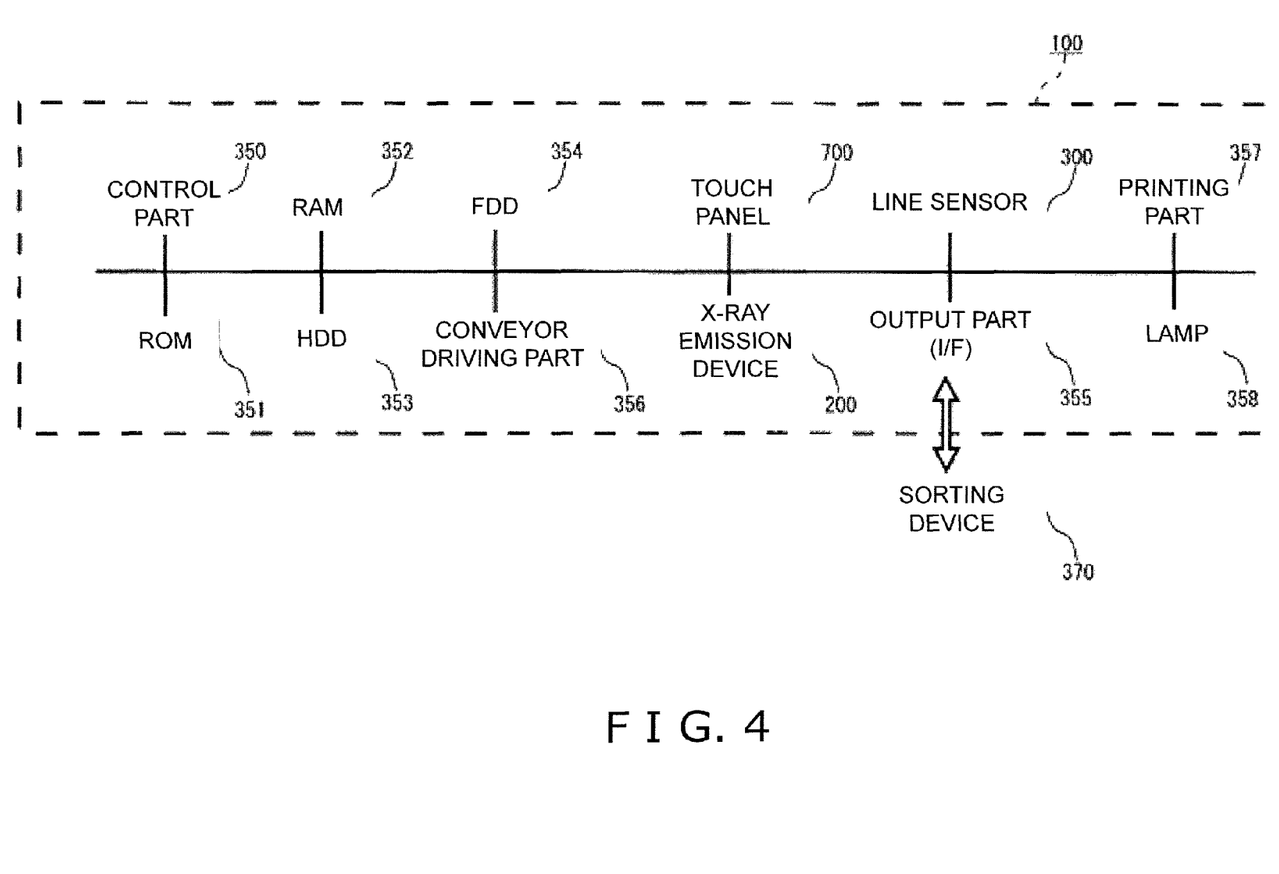
FIG. 4 is a schematic block diagram showing an example of an internal control configuration of the X-ray inspection device.
Figure 5:
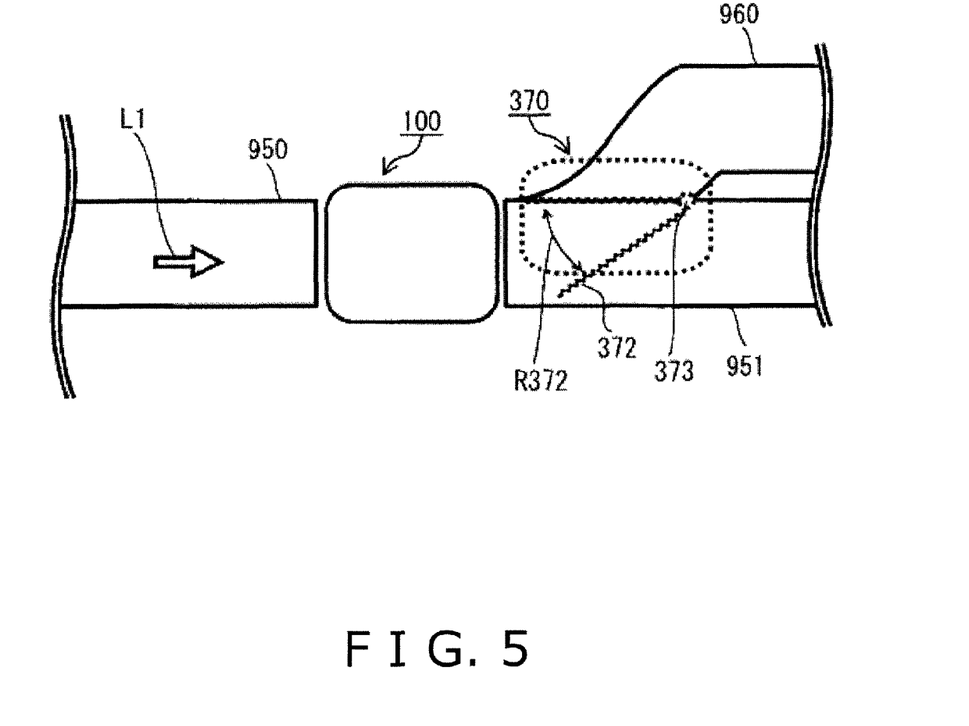
FIG. 5 is a schematic plan view illustrating a pre-process and a post-process of the X-ray inspection device.

FIG. 4 is a schematic block diagram showing an example of an internal control configuration of the X-ray inspection device 100, and FIG. 5 is a schematic plan view illustrating a relationship between a pre-process and a post-process in the X-ray inspection device 100.

As shown in FIG. 4, the X-ray inspection device 100 mainly comprises the X-ray emission device 200, the line sensor 300, a control part 350, a read-only memory (ROM) 351, a random-access memory (RAM) 352, a hard disk drive (HDD) 353, a FLOPPY® disk drive (FDD) 354, an output part (I/F) 355, a conveyor driving part 356 for driving the pair of rollers 810, 811, a printing part 357, a lamp 358, and the touch panel 700.

The control part 350 records a variety of settings information, set by operation of the touch panel 700, onto at least one of the ROM 351, the random-access memory (RAM) 352, the hard disk drive (HDD) 353, and the FLOPPY® disk drive (FDD) 354. The control part 350 then issues, to each of the control configurations, an instruction based on the settings information and a program recorded on at least one of the ROM 351, the random-access memory (RAM) 352, and the hard disk drive (HDD) 353.

For example, the control part 350 instructs the conveyor driving part 356 to drive the pair of rollers 810, 811, instructs the X-ray emission device 200 to emit or stop emitting the X-rays S1, and detects output from the line sensor 300. Thus, the control part 350 preferably constitutes an X-ray detecting unit configured and arranged to detect a level of X-rays passing through an article in a single scanning step as depicted in FIGS. 2, 3 and 4. The control part 350 then records an X-ray inspection history onto one or more of the ROM 351, the random-access memory (RAM) 352, the hard disk drive (HDD) 353, and the FLOPPY® disk drive (FDD) 354. The control part 350 also instructs the printing part 357 to print out the X-ray inspection history as a hardcopy.

The control part 350 also instructs the output part (interface: I/F) 355 to output a signal according to the result of the X-ray inspection and issues an instruction to a sorting device 370 on the exterior of the X-ray inspection device 100. Thus, the control part 350 preferably constitutes an output unit configured and arranged to output a result of determination made by the determining unit. The instruction issued to the sorting device 370 will be described in detail further below. The control part 350 also issues a signal to the lamp 358 according to operational status and the result of the X-ray inspection, and causes the lamp 358 to illuminate continuously or intermittently. For example, a red lamp may be caused to blink in an instance such as one described further below where the production line requires stopping.

As shown in FIG. 5, the X-ray inspection device 100 according to the present embodiment comprises a pre-process conveyor belt 950 and a post-process conveyor belt 951. A branching conveyor belt 960 is connected to the post-process conveyor belt 951, and the sorting device 370 is provided at a branch point between the conveyor belt 951 and the branching conveyor belt 960.

A shaft 373 and a partition 372 are provided to the sorting device 370. The partition 372 rotates about the shaft 373 in the direction indicated by an arrow R372, thereby transporting the article 600 to one of the conveyor belt 951 and the branching conveyor belt 960.

The control part 350 preferably constitutes a determining unit configured to determine a state of the article based on a detection level of the X-rays detected by the X-ray detecting unit using a plurality of thresholds including a first threshold and a second threshold for a single determination criterion. For example, in an instance where it is determined by the control part 350 in FIG. 4 that the gray value of the X-ray transmission image is within a range confined by predetermined thresholds (i.e., exceeds a first threshold but falls below a second threshold described further below), it is determined that the foreign object 610 (tiny foreign object) is present in the article 600. Then, a signal is issued from the output part (I/F) 355 to the sorting device 370, and the partition 372 is moved in the direction of arrow R372 to transport the article 600 to the branching conveyor belt 960.

On the other hand, in an instance where it is determined by the control part 350 in FIG. 4 that the gray value of the X-ray transmission image is less than the first threshold described further below, it is determined that the foreign object 610 is not present in the article 600, a signal is outputted from the output part (I/F) 355 to the sorting device 370, the partition 372 is moved in the direction of the arrow R372, and the article 600 is transported to the conveyor belt 951.

A description will now be given for an instance where the control part 350 according to the present invention sets a plurality of thresholds on each level (each determination criterion).

Figure 6:
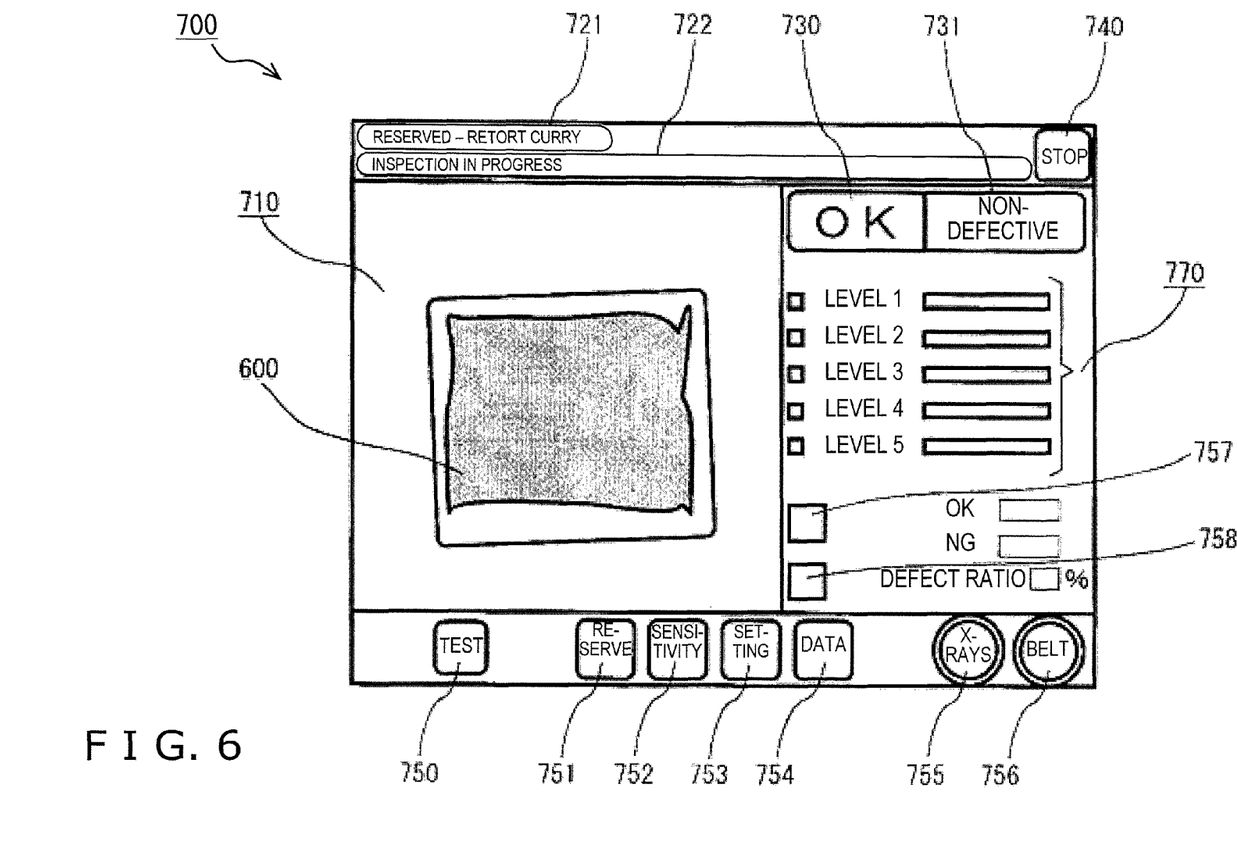
FIG. 6 is a schematic diagram showing an example of a touch panel.
Figure 7:
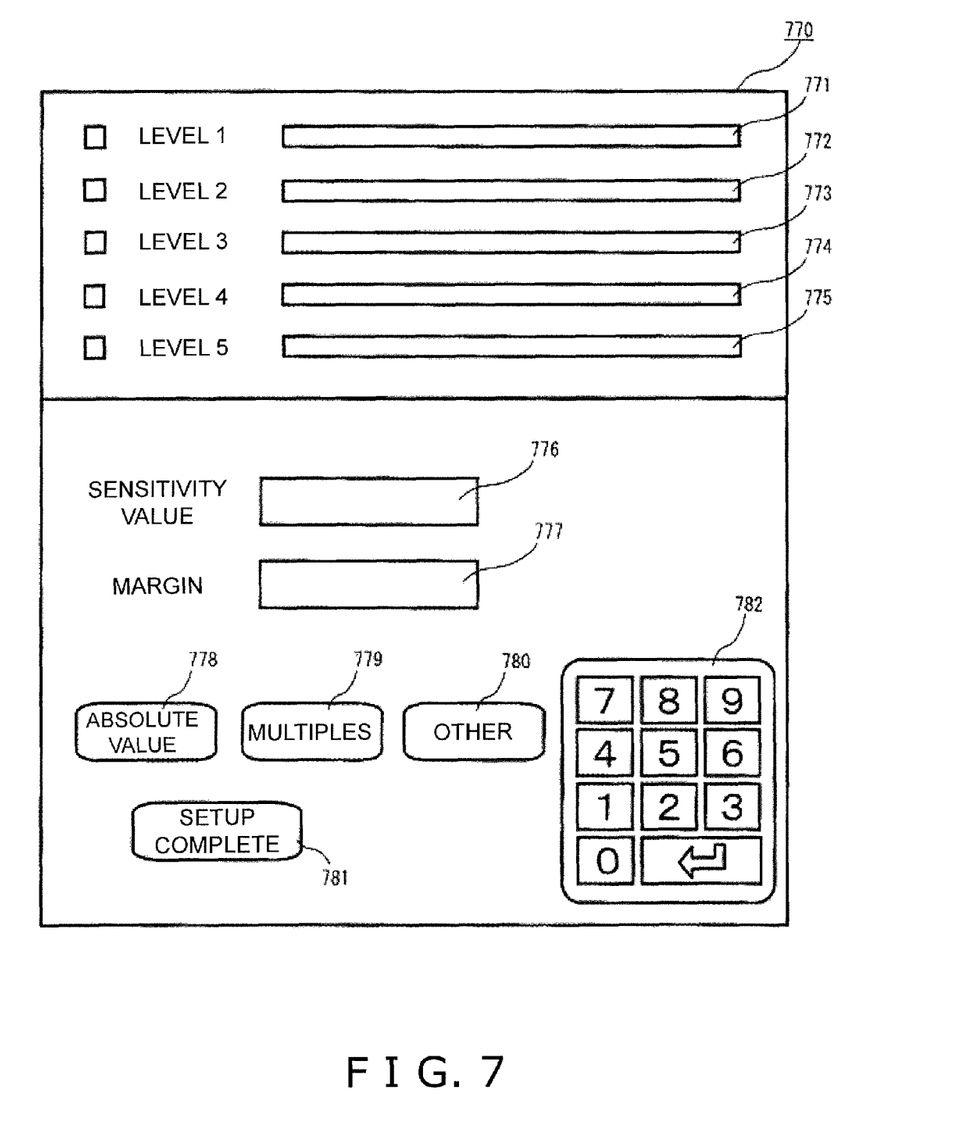
FIG. 7 is a schematic diagram illustrating an example of setting a threshold.
Figure 8:
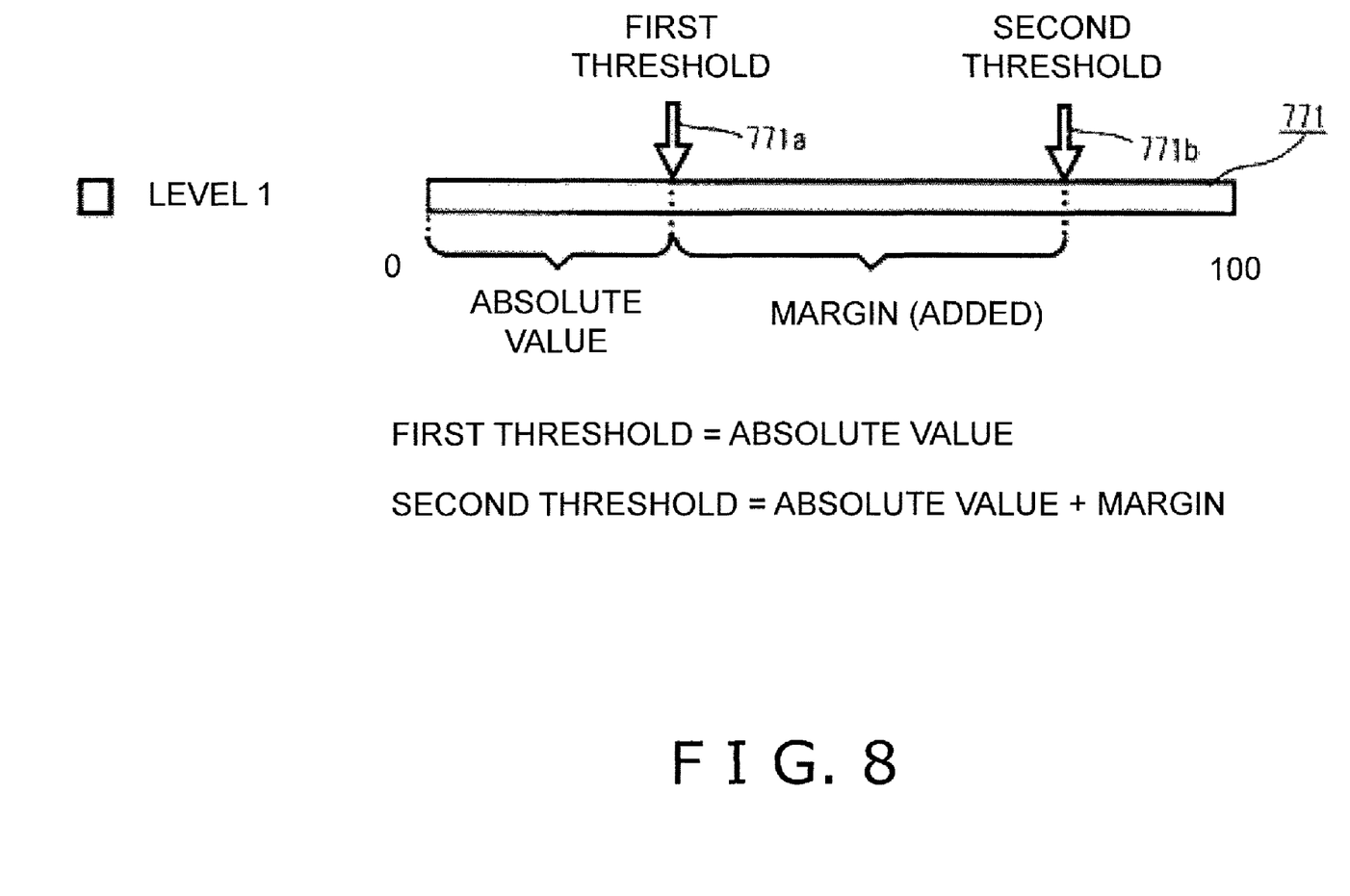
FIG. 8 is a drawing illustrating an overview of an example of a setting shown in FIG. 7.
Figure 9:
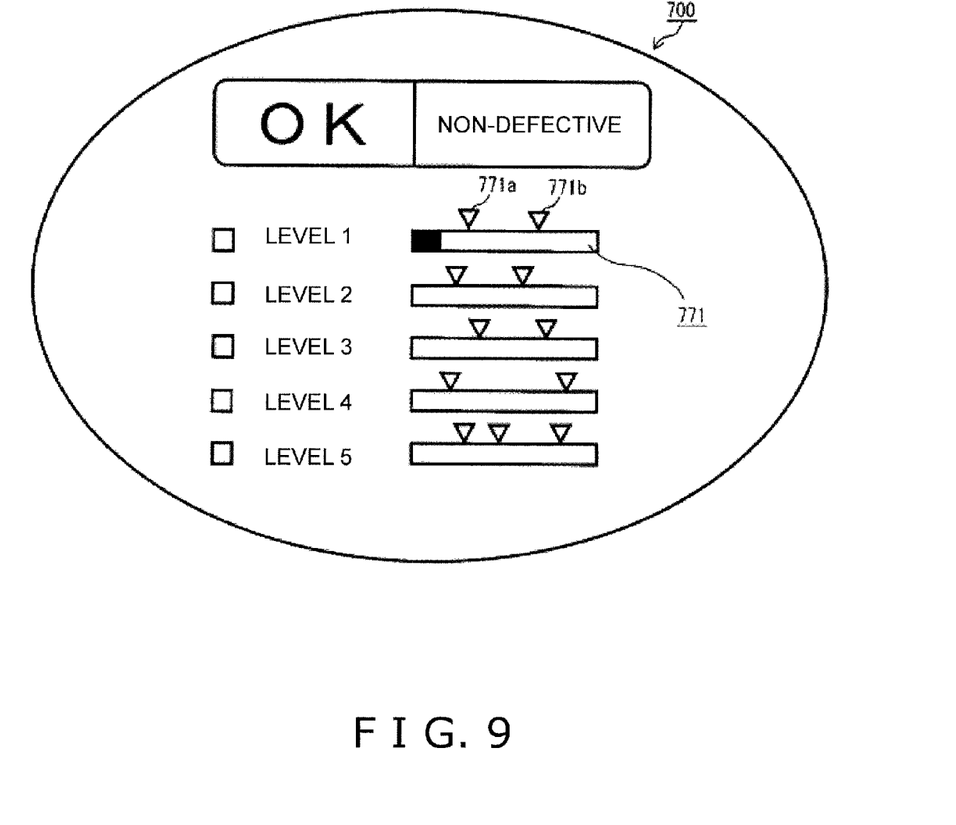
FIG. 9 is a schematic diagram showing an example of a level bar display in FIG. 8.
Figure 10:
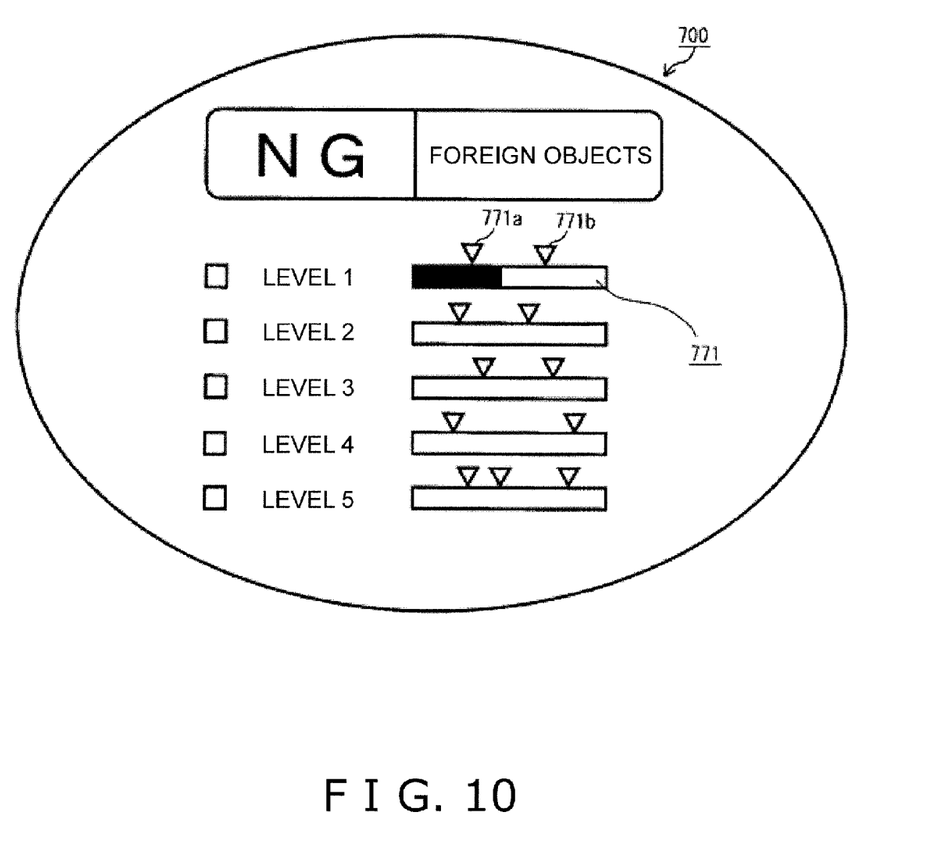
FIG. 10 is a schematic diagram showing an example of a level bar display in FIG. 8.
Figure 11:
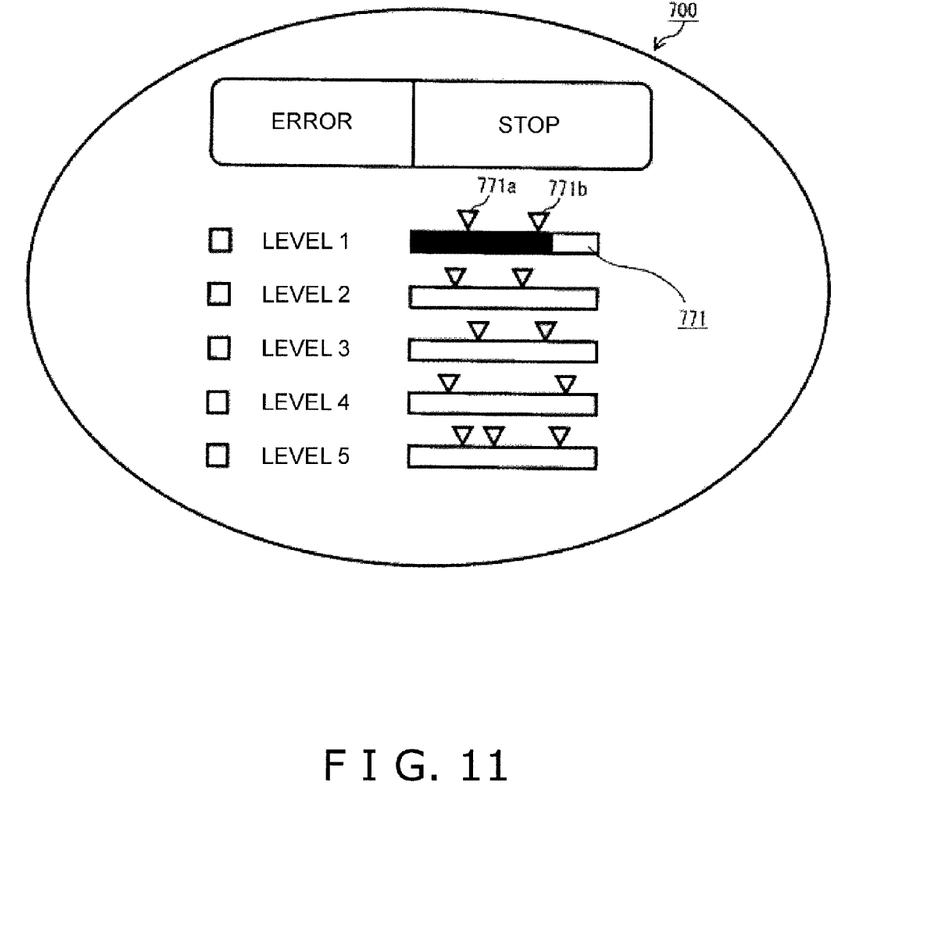
FIG. 11 is a schematic diagram showing an example of a level bar display in FIG. 8.

FIG. 6 is a schematic diagram showing an example of the touch panel 700, FIG. 7 is a schematic diagram illustrating an example of setting a threshold, FIG. 8 is a drawing illustrating an overview of an example of a setting shown in FIG. 7, and each of FIGS. 9 through 11 is a schematic diagram showing an example of a level bar display 771 in FIG. 8.

As shown in FIG. 6, the touch panel 700 comprises a display area 710, display parts 721, 722, 730, 731, an operation stop button 740, a test button 750, a reservation button 751, a sensitivity button 752, a setting button 753, a data button 754, an X-ray button 755, a conveyor belt button 756, an enlarge button 757, an image print button 758, and a thresholds display part 770. The display area 710 is configured to display the X-ray transmission image of the article 600 during X-ray inspection. The display part 721 is configured to display a reservation number. The display part 722 is configured to display states. The display part 730 is configured to display whether or not the inspection was passed. For example, the display part 730 displays that the inspection is "OK" or "NG". The display part 731 is configured to display whether the article 600 is "non-defective" or "defective". The operation stop button 740 is configured to stop operation. The test button 750 is configured to test X-ray emission. The reservation button 751 is configured to reserve a setting for each type of article 600. The sensitivity button 752 is configured to adjust the sensitivity of the line sensor 300. The setting button 753 is configured to set the type of article 600. The data button 754 is configured to output data. The X-ray button 755 is configured to commence X-ray emission. The conveyor belt button 756 is configured to drive the conveyor belt 800. The enlarge button 757 is configured to enlarge the display on the display area 710. The image print button 758 is configured to cause the printing part 357 to print. The thresholds display part 770 is configured to display a variety of thresholds.

As shown in FIG. 6, five inspection methods are provided in the X-ray inspection device 100; namely, level 1, level 2, level 3, level 4, and level 5, each of which represents a different determination criterion. The five inspection methods will now be described.

For example, the inspection methods of levels 1 through 5 include a method for detecting foreign objects based on a point at which the image shade changes and a method for detecting foreign objects based on image binarization. Other inspection methods may further employ a brightness mask, a surroundings mask, or a pattern mask. The brightness mask is configured to set a range of detection of an inspected item based on the brightness of an image obtained by inspection. The surroundings mask is configured to mask the surroundings of the inspected item and to set a range to be inspected. The pattern mask is configured to mask an area having a predetermined pattern so that the area is not detected as foreign objects. Such a mask or a similar function can be applied to adjust the sensitivity of detection to define different determination criterions.

Subsequently pressing the sensitivity button 752 on FIG. 6 causes the thresholds display part 770 shown in FIG. 7 to be displayed on the touch panel 700.

As shown in FIG. 7, the thresholds display part 770 has level bars 771, 772, 773, 774, 775, a sensitivity value box 776, a margin box 777, an absolute value button 778, a multiples button 779, an "other" button 780, a setup complete button 781, and numeric input buttons 782. The level bar 771 is for showing a threshold for level 1. The level bar 772 is for showing a threshold for level 2. The level bar 773 is for showing a threshold for level 3. The level bar 774 is for showing a threshold for level 4. The level bar 775 is for showing a threshold for level 5. The sensitivity value box 776 is for inputting a sensitivity value. The margin box 777 is for inputting a margin value. The absolute value button 778 is for selecting a setting that uses absolute values as a standard. The multiples button 779 is for selecting a setting that uses multiples as a standard. The "other" button 780 is for selecting a setting that uses another standard. The setup complete button 781 is for indicating setup is complete. The numeric input buttons 782 are for inputting a value into the sensitivity value box 776 and the margin box 777.

In the present embodiment, as shown in FIG. 8, a first threshold 771a and a second threshold 771b can be configured for the level bar 771 for level 1. For example, in an instance where the absolute value button 778 in FIG. 7 is pressed, a value inputted into the sensitivity value box 776 is inputted as the first threshold 771a, and the sum of the value inputted into the sensitivity value box 776 and a value inputted into the margin box 777 is set as the second threshold 771b, as shown in FIG. 8.

Specifically, the first threshold 771a is a value for detecting the foreign objects 610 present in the article 600, and the second threshold 771b is a value for an instance where a component from a production line or similar material is present in the article 600 or a component on its own from the production line is separately detected on the conveyor belt 801.

Therefore, in an instance where an article 600 that does not contain foreign objects 610 is transported through the X-ray inspection device 100, the control part 350 displays the level bar 771 for level 1 on the touch panel 700 so as to represent a level lower than the first threshold 771a as shown in FIG. 9, and causes the article 600 to be ejected via the conveyor belt 951.

In an instance where an article 600 containing foreign objects 610 is transported through the X-ray inspection device 100, the control part 350 displays the level bar 771 for level 1 on the touch panel 700 so as to represent a level higher than the first threshold 771a and lower than the second threshold 771b, as shown in FIG. 10. The control part 350 further causes the display part 730 and the display part 731 to display "NG" and "Foreign objects". Furthermore, the control part 350 output a signal to the sorting device 370 through the output part (I/F) 355 to eject the article 600 via the branching conveyor belt 960. This process enables the article 600 containing the foreign objects 610 to be transported to a different location from the normal article 600 without stopping the production line.

In an instance where an article 600 containing a bolt, a nut, or another component from the production line is transported through the X-ray inspection device 100, or in an instance where a bolt, a nut, or another component from the production line is transported by itself through the X-ray inspection device 100, the control part 350 displays the level bar 771 for level 1 on the touch panel 700 so as to represent a level higher than the first threshold 771a and the second threshold 771b, as shown in FIG. 11. The control part 350 further causes the display part 730 and the display part 731 to display "Error" and "Stop"; and issues an instruction to the conveyor driving part 356 to stop driving the conveyor belt 800. This allows the operator to perform an inspection of the component affecting the production line and resolve any problems with the production line.

Accordingly, with the embodiment described above, since a plurality of thresholds is provided for a single determination criterion (e.g., each of levels 1 to 5), it is possible for the control part 350 to make a plurality of determinations according to the detection level of the X-rays. It is therefore possible to recognize that there is a large deviation in the state of the article with respect to the determination criterion in an instance where a large deviation exists, and to recognize that there is a moderate deviation in the state of the article with respect to the determination criterion in an instance where a moderate deviation exists. It is also possible for the output unit to output a result according to each of the determinations made by the determining unit.

Moreover, the control part 350 is configured to determine the state of the article according to a plurality of determination criterions for determining whether the article is defective, and to independently set a plurality of thresholds for each of the determination criterions.

Therefore, it is possible to make a defect determination for small foreign objects, and a defect determination for large foreign objects, relative to the state of the article. For example, it is possible to determine whether the foreign object is capable of affecting operation of the production line.

In this embodiment, the control part 350 is configured to set the first threshold and the second threshold independently of each other.

In such an instance, since one of the thresholds is determined independently of another threshold, the user is not restricted in regard to setting the individual thresholds.

Moreover, the control part 350 is configured to determine the state of the article differently between an instance where the detection level according to the X-ray detecting unit exceeds the first threshold and an instance where the detection level according to the X-ray detecting unit exceeds the second threshold. More specifically, when the detection level exceeds the first threshold value, the control part 350 determines at the foreign object 610 (tiny foreign object) is present in the article 600. On the other hand, when the detection level exceeds the second threshold value, the control part 350 determines that a component from a production line or similar material is present in the article 600 or a component on its own from the production line is separately detected on the conveyor belt 801. Therefore, result outputted by the output unit may be made to differ.

In the X-ray inspection device according to the present invention, the determining unit is able to make a plurality of determinations according to the detection level of the article state. Therefore, in an instance where there is a large deviation in the state of the article with respect to the determination standard, it is possible to recognize that a large deviation exists. Specifically, it is possible to reliably and readily judge whether the foreign objects would affect the production line.

It is therefore possible for the output means to output a result according to each of the determinations made by the determining unit.

Modified Example

Figure 12:
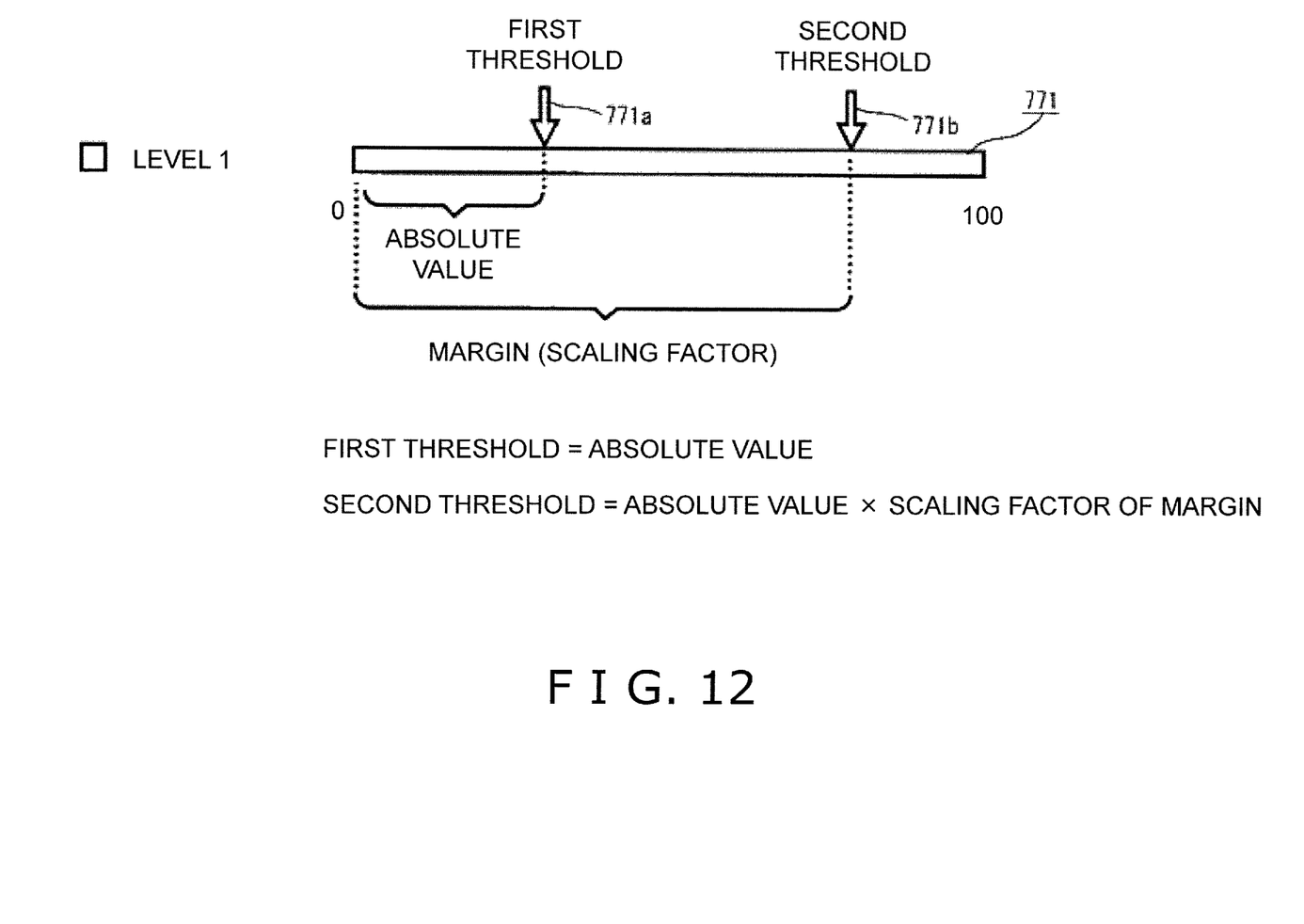
FIG. 12 is a drawing for illustrating an overview of another example of a setting shown in FIG. 7.

FIG. 12 is a drawing for illustrating an overview of another example of a setting shown in FIG. 7.

As shown in FIG. 12, a first threshold 771a and a second threshold 771b can be set for the level bar 771 for level 1. For example, in an instance where the multiples button 779 in FIG. 7 is pressed, a value inputted into the sensitivity value box 776 is inputted as the first threshold 771a, and the product of a value inputted into the margin box 777 and the value inputted into the sensitivity value box 776 is set as the second threshold 771b, as shown in FIG. 12. The first threshold 771a and the second threshold 771b can thereby be set with ease.

In other words, the control part 350 is configured to set the second threshold to be a proportional value of the first threshold in this modified embodiment.

In such an instance, since one of the thresholds may be set as a proportion of another threshold, it can be set automatically by setting the other threshold. The user can therefore readily set a plurality of thresholds.

As shown in level 5 in FIGS. 9 through 11, a third threshold 771c may be provided in addition to the first threshold 771a and the second threshold 771b. In such an instance, pressing the "other" button 780 in FIG. 7 forms a first sensitivity value box and a second sensitivity value box. A numeric value entered in the first sensitivity value box is set as the first threshold. A numerical value entered in the second sensitivity value box is set as the second threshold. Here, the sum of the first threshold and the second threshold may be set as the third threshold. Further, the third threshold may be set by an addition of the margin to the sum of the first sensitivity value and the second sensitivity value. Further, the third threshold may be set by the product of the first sensitivity value and the margin, or the product of the second sensitivity value and the margin.

Up/down buttons may be provided instead of the numeric input buttons 782 for inputting a value into the sensitivity value box 776 and the margin box 777, so that the first threshold 771a, the second threshold 771b, and the third threshold 771c can be finely adjusted.

Since the first threshold 771a and the second threshold 771b are provided for each of level 1, level 2, level 3, level 4, and level 5 as described above, the control part 350 can make a plurality of decisions according to the detection level of the state of the article 600. For example, in an instance where the control part 350 determines according to the detection level of the state of the article 600 that the production line may be affected, the production line can be stopped and inspection and maintenance can be performed. Also, in an instance where the control part 350 determines according to the detection level of the state of the article 600 that only the article 600 needs to be removed, the sorting device 370 can be used to move the article 600 to a location different from where a normal article 600 is transported.

The instances where the gray value of the X-ray transmission image is within a range confined by predetermined thresholds may include an instance where the gray value is equal to or higher than the first threshold and the gray value is equal to or lower than the second threshold, in addition to an instance where the gray value exceeds the first threshold but falls below the second threshold. Also, it may be determined that the foreign object 610 is not included in an instance where the gray value is equal to or lower than the first threshold, in addition to the instance where the gray value is below the first threshold. In the present embodiment, the X-rays S1 corresponds to the X-rays, the article 600 corresponds to the article to be transported; the X-ray inspection device 100 corresponds to the X-ray inspection device; the line sensor 300 corresponds to the X-ray detecting means; levels 1 through 5 correspond to the detection level; the control part 350 corresponds to the determining unit; the output part 355 corresponds to the output means; the first threshold 771a and the second threshold 771b correspond to the thresholds representing the standard for determination by the determining unit; the control part 350 in relation to level 1 corresponds to the same determining unit; the control part 350 for each of levels 2 through 5 corresponds to the same determining unit; the control part 350 corresponds to the defect determining unit; and the instance where the control part 350 stops the production line and the instance where the control part 350 issues an instruction to the sorting device 370 correspond to different results of determination.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. The term "detect" as used herein to describe an operation or function carried out by a component, a section, a device or the like includes a component, a section, a device or the like that does not require physical detection, but rather includes determining, measuring, modeling, predicting or computing or the like to carry out the operation or function.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the embodiments according to the present invention are provided for illustration only, and not for the purpose of limiting the invention as defined by the appended claims and their equivalents.

What is claimed is:
1. An X-ray inspection device comprising:
an X-ray detecting unit configured and arranged to detect a level of X-rays passing through an article on a conveyor in a single scan of the article;
a determining unit configured to determine presence of a foreign object within the article in response to the level of the X-rays detected by the X-ray detecting unit during the single scan of the article, the determining unit defining a plurality of thresholds including a first threshold value and a second threshold value;
a control unit configured and arranged to output a result of determination made by the determining unit; and
a sorting device coupled to the control unit and the determining unit, the control unit being configured such that:
in response to the level of the X-rays detected below the first threshold during the single scan of the article, the control unit operates the sorting device to maintain the article on the conveyor;
in response to the level of the X-rays detected exceeding the first threshold value but being below the second threshold value during the single scan of the article the control unit operates the sorting device to remove the article from the conveyor; and
in response to the level of the X-rays detected exceeding the first threshold value and exceeding the second threshold value during the single scan of the article the control unit stops driving the conveyor.
2. The X-ray inspection device according to claim 1, wherein
the determining unit is configured to determine whether the article is defective.
3. The X-ray inspection device according to claim 1, wherein
the determining unit is configured to set the second threshold to be a proportional value of the first threshold.
4. The X-ray inspection device according to claim 1, wherein
the determining unit is configured to set the first threshold and the second threshold independently of each other.
5. The X-ray inspection device according to claim 1, wherein
the determining unit is configured to determine to receive operator inputted values the first threshold value and the second threshold value.
6. An X-ray inspection device comprising:
an X-ray detecting unit having an X-ray emission device and a single line sensor that detects a level of X-rays emitted from the X-ray emission device that have passed through an article on a conveyor;
a determining unit configured to determine presence of a foreign object within the article in response to the level of the X-rays detected by the single line sensor, the determining unit defining a plurality of thresholds including a first threshold value and a second threshold value;
a control unit configured and arranged to output a result of determination made by the determining unit; and
a sorting device coupled to the control unit and the determining unit, the control unit being configured such that:
in response to the level of the X-rays detected by the single line sensor below the first threshold, the control unit operates the sorting device to maintain the article on the conveyor;
in response to the level of the X-rays detected by the single line sensor exceeding the first threshold value but being below the second threshold value the control unit operates the sorting device to remove the article from the conveyor; and
in response to the level of the X-rays detected by the single line sensor exceeding the first threshold value and exceeding the second threshold value the control unit stops driving the conveyor.

7. The X-ray inspection device according to claim 6, wherein the determining unit is configured to determine whether the article is defective.

8. The X-ray inspection device according to claim 6, wherein
the determining unit is configured to set the second threshold to be a proportional value of the first threshold.

9. The X-ray inspection device according to claim 6, wherein
the determining unit is configured to set the first threshold and the second threshold independently of each other.

10. The X-ray inspection device according to claim 6, wherein
the determining unit is configured to determine to receive operator inputted values the first threshold value and the second threshold value.

11. An X-ray inspection device comprising:
an X-ray detecting unit configured and arranged to detect a level of X-rays passing through an article on a conveyor;
a determining unit configured to determine presence of a foreign object within the article in response to the level of the X-rays detected by the X-ray detecting unit, the determining unit defining a plurality of thresholds including a first threshold value and a second threshold value, with the second threshold set to be a proportional value of the first threshold;
a control unit configured and arranged to output a result of determination made by the determining unit; and
a sorting device coupled to the control unit and the determining unit, the control unit being configured such that:
in response to the level of the X-rays detected below the first threshold, the control unit operates the sorting device to maintain the article on the conveyor;
in response to the level of the X-rays detected exceeding the first threshold value but being below the second threshold value the control unit operates the sorting device to remove the article from the conveyor; and
in response to the level of the X-rays detected exceeding the first threshold value and exceeding the second threshold value the control unit stops driving the conveyor.

12. The X-ray inspection device according to claim 11, wherein
the determining unit is configured to determine whether the article is defective.

13. The X-ray inspection device according to claim 11, wherein
the determining unit is configured to set the first threshold and the second threshold independently of each other.

14. The X-ray inspection device according to claim 11, wherein
the determining unit is configured to determine to receive operator inputted values the first threshold value and the second threshold value.

* * * * *